(12) United States Patent
Kolb

(10) Patent No.: US 9,358,347 B2
(45) Date of Patent: Jun. 7, 2016

(54) SAFETY SYRINGE HAVING AN AUTOMATIC ACTIVATED RETRACTABLE NEEDLE

(75) Inventor: Matthew L. Kolb, Upper Black Eddy, PA (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 0 days.

(21) Appl. No.: 13/491,830

(22) Filed: Jun. 8, 2012

(65) Prior Publication Data

US 2012/0316467 A1 Dec. 13, 2012

Related U.S. Application Data

(60) Provisional application No. 61/494,632, filed on Jun. 8, 2011.

(51) Int. Cl.
| | |
|---|---|
| *A61B 5/00* | (2006.01) |
| *A61M 5/32* | (2006.01) |
| *A61B 5/15* | (2006.01) |
| *A61J 1/20* | (2006.01) |
| *A61B 5/153* | (2006.01) |
| *A61M 5/315* | (2006.01) |

(52) U.S. Cl.
CPC ............ *A61M 5/322* (2013.01); *A61B 5/15003* (2013.01); *A61B 5/153* (2013.01); *A61B 5/150236* (2013.01); *A61B 5/150244* (2013.01); *A61B 5/150404* (2013.01); *A61B 5/150519* (2013.01); *A61B 5/150633* (2013.01); *A61B 5/150885* (2013.01); *A61J 1/2096* (2013.01); *A61B 5/150534* (2013.01); *A61M 5/31511* (2013.01); *A61M 5/3221* (2013.01); *A61M 5/3291* (2013.01); *A61M 5/3293* (2013.01); *A61M 2005/323* (2013.01); *A61M 2005/3224* (2013.01); *A61M 2005/3231* (2013.01)

(58) Field of Classification Search
CPC ... A61B 5/1405; A61B 5/15003; A61B 5/153
USPC .................................................. 600/573, 578
See application file for complete search history.

(56) References Cited

U.S. PATENT DOCUMENTS

| | | |
|---|---|---|
| 5,201,718 A | 4/1993 | Whisson |
| 5,374,250 A | 12/1994 | Dixon |
| 5,782,804 A | 7/1998 | McMahon |

(Continued)

FOREIGN PATENT DOCUMENTS

| | | |
|---|---|---|
| EP | 1911480 A1 | 4/2008 |

*Primary Examiner* — Sean Dougherty
*Assistant Examiner* — Daniel Cerioni
(74) *Attorney, Agent, or Firm* — The Webb Law Firm

(57) ABSTRACT

A syringe assembly for fluid collection includes a housing having a sidewall defining a hollow bore therein, and an elongate plunger with the distal end of the plunger forming a chamber within the hollow bore for containing a fluid therein. The plunger is adapted for slideable movement within the hollow bore between an initial position and a retracted position. The assembly includes a hub disposed at least partially within the hollow bore and at least partially supporting a cannula therewith. The hub is adapted to automatically transition from an initial position in which at least a portion of the cannula is disposed external to the housing, to a retracted position in which the cannula is fully shielded by the housing, upon transition of the elongate plunger from the initial position to the retracted position.

9 Claims, 2 Drawing Sheets

(56) References Cited

U.S. PATENT DOCUMENTS

| | | |
|---|---|---|
| 5,836,921 A | 11/1998 | Mahurkar |
| 5,931,813 A | 8/1999 | Liu |
| 5,964,735 A | 10/1999 | Alexander |
| 6,074,370 A | 6/2000 | Pressly, Sr. et al. |
| 6,117,107 A | 9/2000 | Chen |
| 6,156,013 A | 12/2000 | Mahurkar |
| 6,530,903 B2 | 3/2003 | Wang et al. |
| 6,767,335 B1 | 7/2004 | Helg |
| 7,056,306 B1 | 6/2006 | Halseth et al. |
| 2002/0107488 A1 | 8/2002 | Ranford |

SAFETY SYRINGE HAVING AN AUTOMATIC ACTIVATED RETRACTABLE NEEDLE

CROSS-REFERENCE TO RELATED APPLICATION

This application claims priority to U.S. Provisional Patent Application Ser. No. 61/494,632 filed Jun. 8, 2011, the entire disclosure of which is hereby incorporated by reference.

BACKGROUND OF THE INVENTION

1. Field of the Invention

The subject invention relates to a device for withdrawing a fluid specimen from a patient and subsequently dispensing the collected fluid into a collection container. More particularly, this invention relates to a safety syringe for withdrawing a fluid specimen, such as blood, from a patient, retracting the needle element of the device into the housing of the device, and subsequently dispensing the collected fluid into a separate collection container.

2. Description of Related Art

Hypodermic syringes are widely used in the medical arts for withdrawing fluid samples from a patient. Generally, hypodermic syringes have a metal needle that has a sharpened distal point for penetrating a patient's skin that is either fixedly or removably attached to a housing. With the recognition of fluid borne diseases that are transmitted by bodily fluids, and greater sensitivity of the need to protect healthcare workers from inadvertent contact with previously used needles (commonly referred to as "sharps"), as well as the need to reduce criminal misuse of improperly disposed needles and syringes, syringes that include provisions to prevent reuse and reduce exposure to healthcare workers have been developed.

A variety of shielding mechanisms have also been developed to reduce the incidence of inadvertent exposure of healthcare workers to sharps, however, most of these devices can be compromised by an individual determined to obtain and misuse a hypodermic syringe after its intended use. As a result, further developments in the art of hypodermic syringes have resulted in the advent of hypodermic syringes having needles that withdraw into the body of the syringe once their intended use is completed.

Most of the conventional syringe assemblies in which the needle is withdrawn into the body of the syringe require manufacture and assembly of parts with tight tolerance requirements. Many of the designs depend upon a careful application of forces by the practitioner to draw and/or expel fluids from the syringe. In these assemblies, deviance from the tight tolerances of the multiple components of the device during manufacture and assembly may result in premature activation of the retraction function of the syringe. In addition, conventional syringe assemblies, including a retraction aspect, have been developed for the limited purpose of injecting a medication into a patient, and do not address the need for a syringe used for bodily fluid collection having a retraction element.

Current conventional syringes are considered by users to be virtually fault-free and reliable. They are used for a variety of different procedures involving both "one-shot" fill and inject procedures, as well as more complex mixing, measuring, and delivery functions. In order for a retractable syringe to displace these functional, utilitarian, and reliable conventional syringes, the new retractable syringe should not interfere with current practices, should be cost-effective, and must be substantially reliable. Current conventional syringes are often manufactured at rates of several hundred per minute and their cost is generally not a significant factor in their usage. One skilled in the art of high volume manufacturing recognizes that assembling hundreds of millions of complex retraction syringes having retraction elements contained in a small space, for example on the order of a one-quarter inch diameter bore, is a daunting task.

Accordingly, a need exists for a retractable syringe that is suitable for use as a bodily fluid collection device for subsequent transfer to a collection container. A need further exists for a retractable syringe that is capable of being manufactured at high volumes, and is sufficiently reliable in use when produced at high volume. Such a device is disclosed herein below.

SUMMARY OF THE INVENTION

In accordance with an embodiment of the present invention, a retractable needle assembly for fluid collection includes a housing having a proximal end, a distal end, and a sidewall extending therebetween defining a hollow bore therein. The assembly also includes an elongate plunger having a proximal end and a distal end, with the distal end of the plunger forming a chamber within the hollow bore for containing a fluid therein. The plunger is adapted for slideable movement within the hollow bore between an initial position and a retracted position. The assembly also includes a hub disposed at least partially within the hollow bore and at least partially supporting a cannula therewith. The distal end of the elongate plunger defines an aperture therein for receiving the cannula therethrough. The hub is adapted to automatically transition from an initial position in which at least a portion of the cannula is disposed external to the housing, to a retracted position in which the cannula is fully shielded by the housing, upon transition of the elongate plunger from the initial position to the retracted position.

In certain configurations, the hub is frictionally restrained within the hollow bore by a resistive force. The hub may include a disc which supports the cannula. Optionally, the elongate plunger defines a hole therein adapted to receive a portion of the cannula therethrough. The elongate plunger may also include a stopper connected at the distal end, with the stopper defining a hole therein adapted to receive a portion of the cannula therethrough. The cannula may define a break surrounded by a portion of the sidewall of the housing, and advancement of the elongate plunger in a proximal direction may draw fluid through the break in the cannula and into the chamber.

The hub of the assembly may include a distal surface and the elongate plunger may include a stopper having a proximal surface adapted to contact the distal surface of the hub. Transition of the elongate plunger from the initial position to the retracted position may cause the proximal surface of the stopper to contact the distal surface of the hub at a stopper interface. A force applied to the elongate plunger to transition the elongate plunger from the initial position to the retracted position may be sufficient to advance the stopper interface in a proximal direction within the hollow bore. Advancement of the stopper interface may withdraw the cannula into the hollow bore until the cannula is fully shielded by the housing. The elongate plunger may be redeployed within the housing once the distal surface of the hub and the proximal surface of the stopper are isolated. Optionally, the elongate plunger may be redeployed within the housing independently of the hub to expel fluid from the chamber.

In accordance with another embodiment of the present invention, a retractable needle assembly for fluid collection includes a housing having a proximal end, a distal end, and a sidewall extending therebetween defining a hollow bore therein. The assembly also includes an elongate plunger having a stopper having a proximal end and a distal end connected thereto, with the stopper having a proximal surface and a distal end forming a chamber within the hollow bore for containing a fluid therein. The plunger is adapted for slideable movement within the hollow bore between an initial position and a retracted position. The assembly also includes a hub frictionally restrained within the hollow bore by a resistive force, the hub at least partially supporting a cannula therewith, with the hub having a distal surface. A force applied to the elongate plunger in a proximal direction causes the proximal surface of the stopper to contact the distal surface of the hub. The proximal force is greater than the resistive force such that the resistive force is disrupted and the hub is automatically advanced within the hollow bore of the housing.

In certain configurations, the cannula defines a break surrounded by a portion of the sidewall of the housing and advancement of the elongate plunger in a proximal direction draws fluid through the break in the cannula and into the chamber. Optionally, the cannula includes a patient tip and the resistive force is greater than a penetration force of a patient's skin such that the patient tip may pierce the patient's skin. The resistive force frictionally restraining the hub within the hollow bore may be restored once the force applied to the elongate plunger in the proximal direction is terminated. The elongate plunger may be redeployed within the hollow bore upon application of a force thereto in a distal direction. Optionally, the elongate plunger may be redeployed within the housing independently of the hub to expel fluid from the chamber.

In accordance with another embodiment of the present invention, a retractable needle assembly for fluid collection includes a housing having a proximal end, a distal end, and a sidewall extending therebetween defining a hollow bore therein. The assembly also includes an elongate plunger having a proximal end and a distal end, the distal end of the plunger forming a chamber within the hollow bore for containing a fluid therein, with the plunger adapted for slideable movement within the hollow bore between a first position and a second position. The assembly further includes a hub disposed at least partially within the hollow bore and at least partially supporting a cannula therewith, with the distal end of the elongate plunger defining an aperture therein for receiving the cannula therethrough. Transition of the elongate plunger from the first position to the second position causes the hub to automatically transition from an initial position in which at least a portion of the cannula is disposed external to the housing, to a retracted position in which the cannula is fully shielded by the housing. The hub remains in the retracted position during subsequent transition of the elongate plunger from the second position to the first position.

In certain configurations, the cannula defines a break surrounded by a portion of the sidewall of the housing, and transition of the elongate plunger from the first position to the second position draws fluid through the break in the cannula and into the chamber. Optionally, subsequent transition of the elongate plunger from the second position to the first position expels fluid from the chamber.

Further details and advantages of the invention will become clear from the following detailed description when read in conjunction with the accompanying drawings.

DETAILED DESCRIPTION OF THE INVENTION

Figure 1:
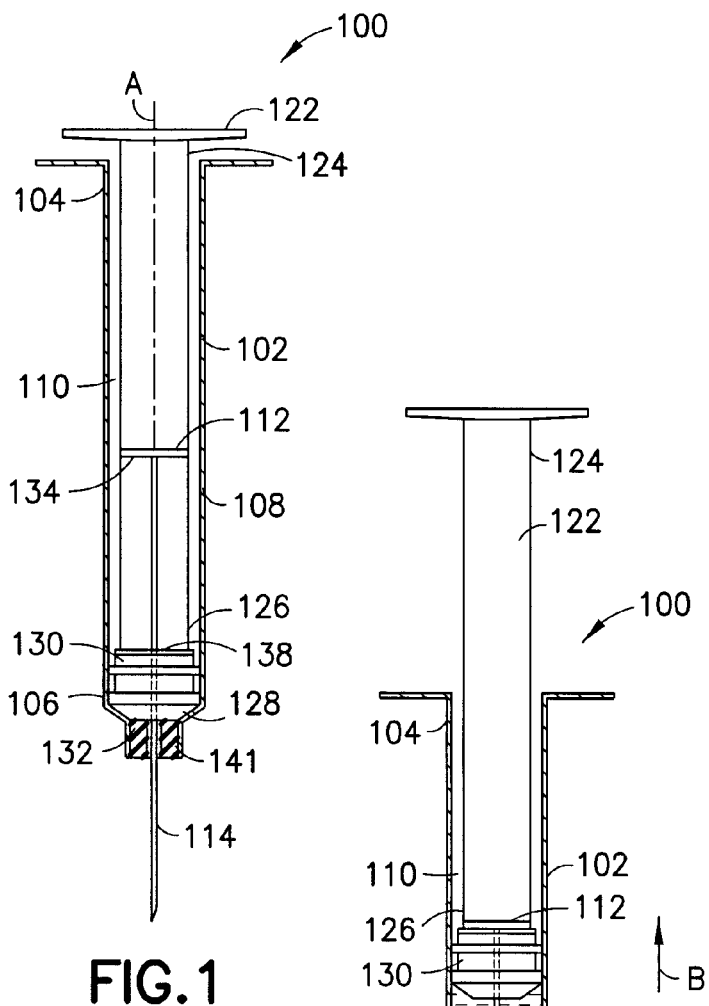
FIG. 1 is a cross-sectional front view of a syringe assembly in an initial position in accordance with an embodiment of the present invention.

For purposes of the description hereinafter, the words "upper", "lower", "right", "left", "vertical", "horizontal", "top", "bottom", "lateral", "longitudinal", and like spatial terms, if used, shall relate to the described embodiments as oriented in the drawing figures. However, it is to be understood that many alternative variations and embodiments may be assumed except where expressly specified to the contrary. It is also to be understood that the specific devices and embodiments illustrated in the accompanying drawings and described herein are simply exemplary embodiments of the invention.

The present invention is directed to a syringe assembly, such as a hypodermic syringe, for the extraction of bodily fluids from a patient, and the subsequent transfer of the extracted fluid to a separate collection container. As shown in FIGS. 1-5, a retractable needle assembly 100 in accordance with an embodiment of the present invention includes a housing 102, such as an elongated cylindrical barrel, having a proximal end 104 and a distal end 106 and a sidewall 108 extending therebetween and defining a hollow bore 110 between the proximal end 104 and the distal end 106. A hub 112 is disposed at least partially within the hollow bore 110 and at least partially supports a needle cannula 114 extending along a longitudinal axis A, as shown in FIG. 1, of the retractable needle assembly 100. In one embodiment, the hub 112 has a disc shape and supports the cannula 114 at the center of the disc. In accordance with certain configurations, the hub 112 is clearance fitted within the interior of the hollow bore 110 such that the hub 112 experiences substantially no frictional resistance with the interior walls of the hollow bore 110. Alternatively, the hub 112 may be frictionally fitted within the hollow bore 110 with a sufficient resistive force such that the tip of the cannula 114 may penetrate the skin of a patient without dislodging the hub 112 and the cannula 114 connected thereto from the initial position of the hub 112.

An elongate plunger 122, having a proximal end 124 and a distal end 126, is disposed and sized to fit within the bore 110 of the housing 102 for a slidable movement therein. The plunger 122 and the sidewall 108 of the housing 102 are dimensioned to define a chamber 128 for receiving and expelling fluids therefrom. In one embodiment, the plunger 122 includes a stopper 130 disposed at the distal end 126 to occlude an open end 132 of the chamber 128, with the stopper 130 being sized and shaped to form a slidably substantially fluid tight seal with the bore 110 of the housing 102 for forming the chamber 128.

Stopper 130 may define a substantially cylindrical hole therein which accommodates the cannula 114 therethrough. Stopper 130 is fitted with the sidewall of the chamber 128 to form a liquid tight seal therewith. In one configuration, the cylindrical hole in stopper 130 is offset from the longitudinal axis A, as shown in FIG. 1, to allow the needle cannula 114 attached to the hub 112 to lie along the longitudinal axis A of the housing 102 and the stopper 130.

The hub 112 has a distal surface 134 adapted for contact with a proximal surface 138 of the stopper 130 of the plunger 122. The stopper 130 is circumferentially disposed about the cannula 114 extending from the hub 112. In use, as will be discussed herein, the stopper 130 may be withdrawn in the proximal direction until the proximal surface 138 of the stopper 130 contacts the distal surface 134 of the hub 112. At this time, the force of the plunger 122 being pulled in the proximal direction is sufficient to dislodge the hub 112 from the initial position of the hub 112, and the hub 112 and the cannula 114 connected thereto are pulled further into the hollow bore 110 in the proximal direction.

When the plunger 122 is redeployed into the hollow bore 110, as will also be discussed herein, the contact between the distal surface 134 of the hub 112 and the proximal surface 138 of the stopper 130 is disrupted and the plunger 122 is free to travel into the hollow bore 110 while the hub 112 remains stationary due to the frictional component of the contact force between the cannula 114 and a seal 141.

In use, a user of the retractable needle assembly 100 would insert the tip of the needle cannula 114 extending from the housing 102 in the initial position, as shown in FIG. 1, into a patient to withdraw a fluid sample, such as a blood specimen. In this orientation, the hub 112 is clearance fit within the hollow bore 110, and the tip of the needle cannula connected thereto extends outwardly from the distal end 106 of the housing 102. Alternatively, the hub 112 is frictionally disposed within the hollow bore 110, and the tip of the needle cannula connected thereto extends outwardly from the distal end 106 of the housing 102.

In one embodiment, the substantially air tight seal 141 is provided around the cannula 114 at the distal end 106 of the housing 102 and the frictional component of the contact force between the cannula 114 and the seal 141 is greater than the force applied on the tip of the cannula 114 by the patient's skin during puncture, thereby retaining the hub 112 in the initial position during patient access. In another embodiment, the frictional resistance between the outer perimeter of the hub 112 and the interior of the sidewall 108 of the housing 102 is greater than the force applied on the tip of the cannula 114 by the patient's skin during puncture, thereby retaining the hub 112 in the initial position during patient access. In another configuration, the substantially air tight seal 141 is provided around the cannula 114 at the distal end 106 of the housing 102 and the frictional resistance of the seal 141 is higher than the force required to penetrate the skin of a patient. In a further configuration, the frictional resistance of the seal 141 is also higher than the friction of the interference between the cannula 114 and the stopper 130 of the plunger 122. The plunger 122 is also provided within the hollow bore 110 of the housing 102 in an initial position such that the stopper 130 is provided substantially within the distal end 106 of the housing 102. In one configuration, the stopper 130 does not contact the hub 112 in the initial position.

Figure 2:
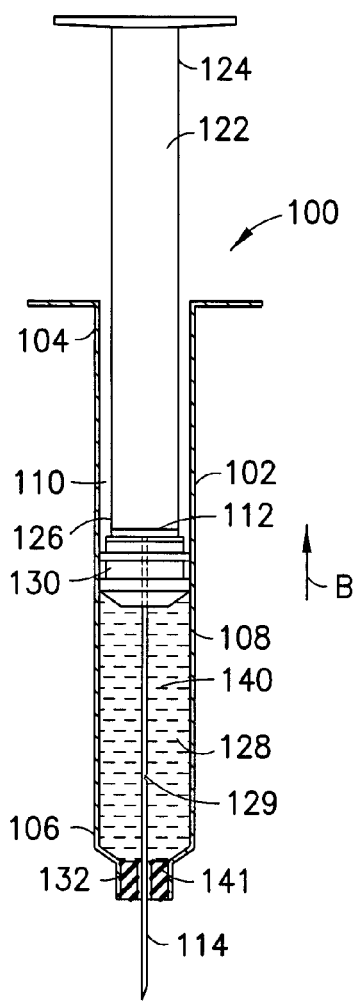
FIG. 2 is a cross-sectional front view of the syringe assembly of FIG. 1 in a partial specimen draw position in accordance with an embodiment of the present invention.
Figure 3:
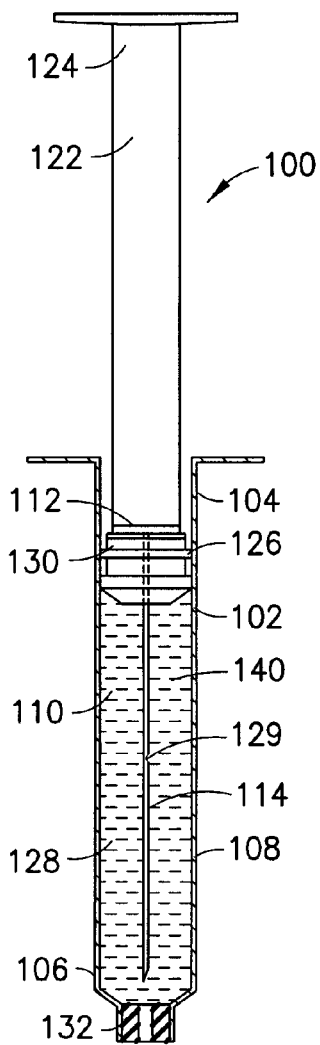
FIG. 3 is a cross-sectional front view of the syringe assembly of FIG. 1 in the retracted position in accordance with an embodiment of the present invention.

As a user pulls the proximal end 124 of the plunger 122 in the direction of arrow B, as shown in FIG. 2, a vacuum is created in the chamber 128 and a fluid sample 140 from the patient is drawn into the chamber 128. A notch 129 in the cannula 114 allows for fluid specimen to exit the interior of the cannula 114 and flow into the chamber 128. As the plunger 122 is withdrawn in the direction of arrow B, the proximal surface 138 of the stopper 130 contacts the distal surface 134 of the hub 112 with sufficient force to dislodge the hub 112 from its initial position and to pull the hub 112 within the hollow bore 110, as shown in FIG. 2, to a location proximal to the initial position. As the hub 112 is advanced within the hollow bore 110, the cannula 114 is retracted into the hollow bore 110. Once the plunger has been withdrawn to the maximum draw position, as shown in FIG. 3, the cannula 114 is completely shielded by the housing 102. The transition from the initial position, shown in FIG. 1, to the retracted position, shown in FIG. 3, occurs automatically upon withdrawal of the plunger 122 during specimen draw, as shown in FIG. 2. In an alternative embodiment, the retractable needle assembly 100 is configured such that the cannula does not start to retract until after the full specimen draw position is reached. For example, a user may draw 5 ml of blood into a syringe as the desired sample collection volume. The user may then remove the needle from the patient's vein and further retract the plunger 122 in order to retract the cannula 114 into the interior of the housing 102. The advantage of this configuration is that the user is aware of exactly when the needle is withdrawn from the patient's vein. This may improve user safety when a user is stabilizing the device within the vein by pressing on the cannula 114 by reducing potential needle-stick injuries. This may also reduce patient pain as the user knows if the cannula 114 is exposed or withdrawn prior to removing the retractable needle assembly 100 from the patient.

Figure 4:
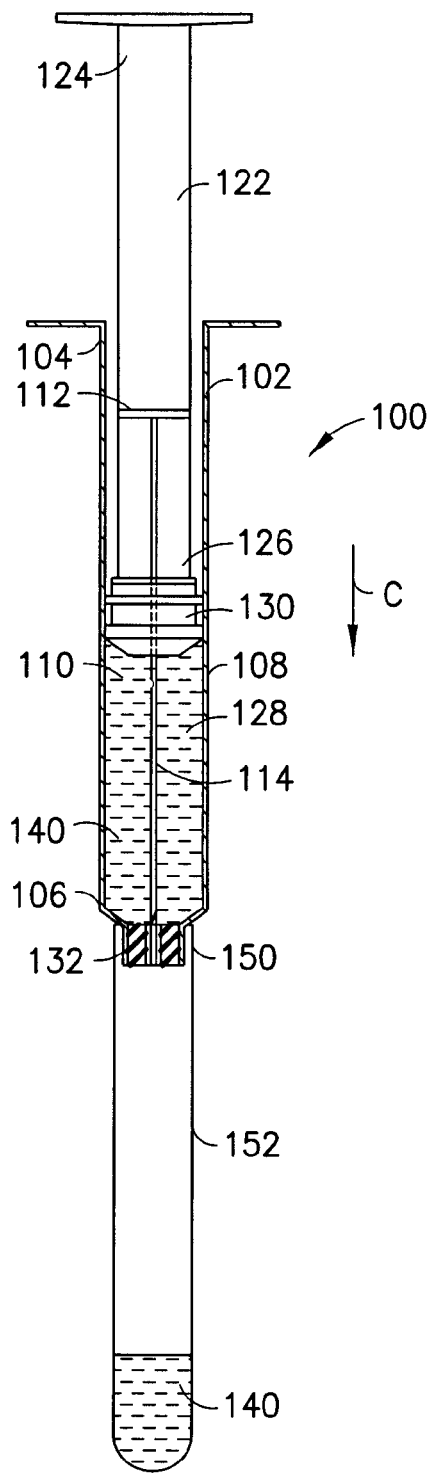
FIG. 4 is a cross-sectional front view of the syringe assembly of FIG. 1 in the specimen transfer position engaged with a specimen collection container in accordance with an embodiment of the present invention.

Once the specimen draw is complete, the user engages the distal end 106 of the retractable needle assembly 100 with an open end 150 of a specimen collection container 152 and transfers the collected fluid specimen 140 from within the chamber 128 into the specimen collection container 152 by redeploying the plunger 122 into the housing 102 in the direction of arrow C, as shown in FIG. 4. As the plunger 122 is redeployed, the stopper 130 travels away from the hub 112 and the cannula 114 is held between the seal 141 and the hub 112. Alternatively, as the plunger 122 is redeployed, the stopper 130 travels away from the hub 112 leaving the hub 112 frictionally engaged with the interior of the sidewall 108 of the housing 102 at a location proximal to the initial position.

Figure 5:
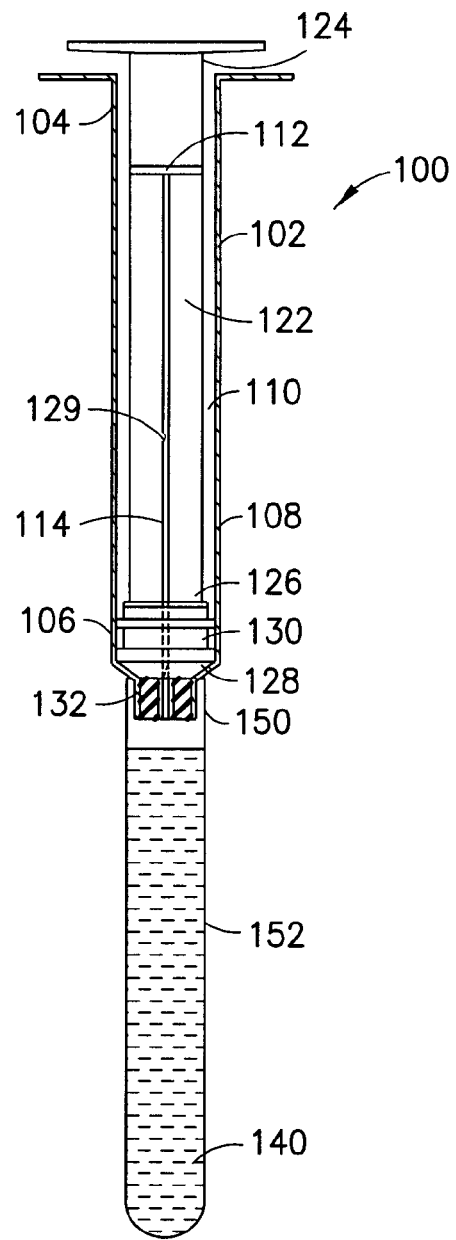
FIG. 5 is a cross-sectional front view of the syringe assembly of FIG. 1 in the fully dispensed position in accordance with an embodiment of the present invention.

As shown in FIG. 5, once the transfer of fluid specimen 140 from the chamber 128 into the collection container 152 is complete, the plunger 122 is fully deployed into the housing 102 and the hub 112 remains at the proximal location within the housing 102 with the cannula 114 fully shielded by the housing 102.

In a further configuration, the seal 141 is aligned with the longitudinal axis A of the housing 102 and stopper 130. When the stopper 130 is stationary at the maximum specimen draw position, and when the plunger 122 is further withdrawn and the cannula 114 retracts, the cannula 114 is forced to bend, like a leaf spring. The cannula 114 is held centrally at each end, between the seal 141 and the hub 112, but is held off-center by the stopper 130. As a result, when the cannula 114 is withdrawn from the seal 141, the cannula 114 experiences a bending moment, which acts to move the position of the tip of the cannula 114 towards the sidewall 108 of the housing 102, which has the effect of constraining the tip of the cannula 114 within the interior of the retractable needle assembly 100 when the plunger 122 is advanced to transfer the sample, and which prevents the cannula 114 from being re-advanced through the seal 141, which effectively renders the retractable needle assembly 100 unable to be re-used.

While the present invention is described with reference to several distinct embodiments of a retractable needle assembly and method of use, those skilled in the art may make modifications and alterations without departing from the scope and spirit. Accordingly, the above detailed description is intended to be illustrative rather than restrictive.

What is claimed is:

1. A retractable needle assembly for fluid collection, comprising:
- a housing having a proximal end, a distal end, and a sidewall extending between the proximal end of the housing and the distal end of the housing, the sidewall defining a hollow bore;
- an elongate plunger having a proximal end and a distal end, the plunger adapted for slideable movement within the hollow bore between an initial plunger position and a retracted plunger position, the elongate plunger having a stopper disposed at the distal end of the plunger, the stopper having a proximal surface, the stopper forming a slidably substantially fluid tight seal with the hollow bore, the stopper and the hollow bore forming a chamber having a proximal end and a distal end for containing a fluid, the distal end of the chamber including an open end including a seal; and
- a hub disposed at least partially within the hollow bore and at least partially supporting a cannula, the distal end of the elongate plunger defining an aperture for receiving the cannula, the hub having a distal surface,
- wherein the hub is adapted to automatically transition from an initial hub position in which at least a portion of the cannula is disposed external to the housing, the seal is provided around the cannula, and the hub is spaced apart from the stopper, to a retracted hub position proximal to the initial position in which the cannula is fully shielded by the housing, upon transition of the elongate plunger from the initial plunger position to the retracted plunger position which causes the proximal surface of the stopper to contact the distal surface of the hub to transition the hub toward the proximal end of the housing from the initial hub position to the retracted hub position, and
- wherein, after transition of the hub to the retracted hub position, the elongate plunger is adapted to be fully redeployed within the housing independently of the hub to expel fluid from the chamber, such that the hub is frictionally restrained in the retracted hub position by a contact force between the cannula and the seal upon full redeployment of the elongate plunger from the retracted plunger position toward the distal end of the housing.

2. The retractable needle assembly of claim 1, wherein the hub comprises a disc which supports the cannula, and wherein the cannula does not extend in the hollow bore proximal of the hub.

3. The retractable needle assembly of claim 1, wherein the elongate plunger defines a hole adapted to receive a portion of the cannula.

4. The retractable needle assembly of claim 1, wherein the stopper defines a hole adapted to receive a portion of the cannula.

5. The retractable needle assembly of claim 1, wherein the cannula defines a break surrounded by a portion of the sidewall of the housing and advancement of the elongate plunger in a proximal direction draws fluid through the break in the cannula and into the chamber.

6. The retractable needle assembly of claim 1, wherein a force applied to the elongate plunger to transition the elongate plunger from the initial plunger position to the retracted plunger position is sufficient to advance the stopper in a proximal direction within the hollow bore.

7. The retractable needle assembly of claim 6, wherein the advancement of the stopper withdraws the cannula into the hollow bore until the cannula is fully shielded by the housing.

8. A retractable needle assembly for fluid collection, comprising:
- a housing having a proximal end, a distal end, and a sidewall extending between the proximal end of the housing and the distal end of the housing, the sidewall defining a hollow bore;
- an elongate plunger having a proximal end and a distal end, the plunger adapted for slideable movement within the hollow bore between a first position and a second position, the elongate plunger having a stopper disposed at the distal end of the plunger, the stopper having a proximal surface, the stopper forming a slidably substantially fluid tight seal with the hollow bore, the stopper and the hollow bore forming a chamber having a proximal end and a distal end for containing a fluid, the distal end of the chamber including an open end including a seal; and
- a hub disposed at least partially within the hollow bore and at least partially supporting a cannula, the distal end of the elongate plunger defining an aperture for receiving the cannula, the hub having a distal surface,
- wherein transition of the elongate plunger from the first position to the second position causes the proximal surface of the stopper to contact the distal surface of the hub to automatically transition the hub toward the proximal end of the housing from an initial position in which at least a portion of the cannula is disposed external to the housing, the seal is provided around the cannula, and the hub is spaced apart from the stopper, to a retracted position proximal to the initial position in which the cannula is fully shielded by the housing, and
- wherein, after transition of the hub to the retracted position, the elongate plunger is adapted to be fully redeployed within the housing independently of the hub to expel fluid from the chamber, such that the hub is frictionally restrained in the retracted position by a contact force between the cannula and the seal during subsequent transition of the elongate plunger from the second position in a direction toward the distal end of the housing to a position at which the elongate plunger is fully deployed into the housing.

9. The retractable needle assembly of claim 8, wherein the cannula defines a break surrounded by a portion of the sidewall of the housing and transition of the elongate plunger from the first position to the second position draws fluid through the break in the cannula and into the chamber.

* * * * *